(12) United States Patent
Miyoshi (10) Patent No.: US 8,540,625 B2
(45) Date of Patent: Sep. 24, 2013

(54) ENDOSCOPE

(71) Applicant: Olympus Medical Systems Corp., Tokyo (JP)

(72) Inventor: Hiroaki Miyoshi, Fuchu (JP)

(73) Assignee: Olympus Medical Systems Corporation, Tokyo (JP)

( * ) Notice: Subject to any disclaimer, the term of this patent is extended or adjusted under 35 U.S.C. 154(b) by 0 days.

(21) Appl. No.: 13/626,493

(22) Filed: Sep. 25, 2012

(65) Prior Publication Data

US 2013/0102960 A1   Apr. 25, 2013

Related U.S. Application Data (63) Continuation of application No. PCT/JP2012/054087, filed on Feb. 21, 2012.

(30) Foreign Application Priority Data

Mar. 29, 2011  (JP) ................................ 2011-073040

(51) Int. Cl.
*A61B 1/00* (2006.01)

(52) U.S. Cl.
USPC ...................................... 600/146; 604/95.04

(58) Field of Classification Search
USPC ........ 604/95.01, 95.04, 95.05, 528; 600/101, 600/146–150
See application file for complete search history.

(56) References Cited

U.S. PATENT DOCUMENTS

| 6,638,213 B2 * | 10/2003 | Ogura et al. ................... 600/148 |
| 6,899,673 B2 * | 5/2005 | Ogura et al. ................... 600/146 |
| 2008/0097159 A1 | 4/2008 | Ishiguro |

FOREIGN PATENT DOCUMENTS

| JP | A 62-292134 | 12/1987 |
| JP | A 4-210039 | 7/1992 |
| JP | A 2000-316803 | 11/2000 |
| JP | A 2004-230189 | 8/2004 |
| JP | A 2004-298446 | 10/2004 |
| JP | A 2009-160211 | 7/2009 |
| JP | A 2010-201 | 1/2010 |
| WO | WO 2006/134881 A1 | 12/2006 |
| WO | WO 2011/040104 A1 | 4/2011 |
| WO | WO 2012/132636 A1 | 10/2012 |

OTHER PUBLICATIONS

Nov. 20, 2012 Office Action issued in Japanese Patent Application No. 2012-543833 (with translation).
Mar. 27, 2012 Search Report issued in International Patent Application No. PCT/JP2012/054087 (with translation).

* cited by examiner

*Primary Examiner* — Theodore Stigell
(74) *Attorney, Agent, or Firm* — Oliff & Berridge, PLC (57) ABSTRACT

An endoscope includes an insertion portion, a bending operation input portion, a first bending drive mechanism and a second bending drive mechanism. The insertion portion includes a first bending portion and a second bending portion disposed at the proximal end of the first bending portion. The bending operation input portion can bend the first bending portion. The first bending drive mechanism bends the first bending portion in accordance with the operation of the bending operation input portion. The second bending drive mechanism can automatically bend the second bending portion in the same direction as the bending direction of the first bending portion in conformity to the first bending portion after the start of the bending of the first bending portion.

5 Claims, 7 Drawing Sheets

ENDOSCOPE

CROSS-REFERENCE TO RELATED APPLICATIONS

This is a Continuation Application of PCT Application No. PCT/JP2012/054087, filed Feb. 21, 2012, which was published under PCT Article 21 (2) in Japanese.

This application is based upon and claims the benefit of priority from the prior Japanese Patent Application No. 2011-073040, filed Mar. 29, 2011, the entire contents of which are incorporated herein by reference.

BACKGROUND OF THE INVENTION

1. Field of the Invention

This invention relates to an endoscope having a plurality of bending portions.

2. Description of the Related Art

Jpn. Pat. Appln. KOKAI Publication No. 2009-160211 has disclosed an endoscope which allows one of two knobs of an operation portion to be moved along the axial direction of the knobs so that the two knobs are interlocked or individually operable. When the two knobs are interlocked, first and second bending portions can be bent at the same time. When the two knobs are individually operable, the first bending portion and the second bending portion can be separately bent.

Jpn. Pat. Appln. KOKAI Publication No. 2010-201 has disclosed an endoscope including a first bending portion which vertically bends, and a second bending portion which horizontally bends together with the first bending portion. That is, if the first bending portion is bent, for example, upward, the second bending portion bends, for example, leftward at the same time.

When an endoscope including not only a first bending portion but also a second bending portion is used, it is generally possible to improve the performance of the insertion of an insertion portion into an insertion target such as a large intestine.

For example, when the insertion portion of the endoscope is inserted to the far side of the large intestine from the anus side, a surgeon generally holds and operates the insertion portion of the endoscope with the left hand, and firmly holds the insertion portion with the right hand to rotate the insertion portion around the axis or axially move the insertion portion. When the insertion portion is inserted in the large intestine to some degree, the surgeon preferably keeps holding the insertion portion without taking the right hand off the insertion portion to stabilize the position of the insertion portion while feeling the insertion into the large intestine.

BRIEF SUMMARY OF THE INVENTION

An endoscope according to the invention includes an insertion portion which includes a first bending portion and a second bending portion disposed at the proximal end of the first bending portion; a bending operation input portion which is configured to bend the first bending portion; a first bending drive mechanism which is configured to bend the first bending portion in accordance with the operation of the bending operation input portion; and a second bending drive mechanism which is configured to automatically bend the second bending portion in the same direction as the bending direction of the first bending portion in conformity to the first bending portion after the start of the bending of the first bending portion.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of this invention will be described with reference to the drawings.

The first embodiment is described with reference to FIG. 1 to FIG. 6B.

Figure 1:
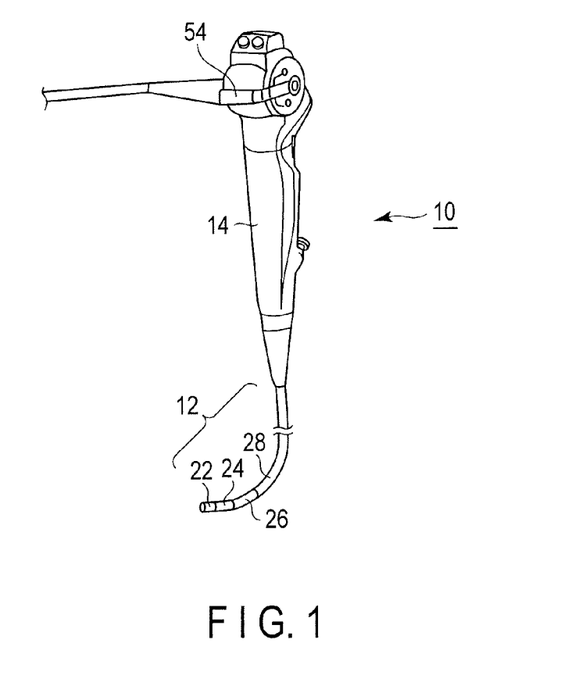
FIG. 1 is a schematic diagram showing an endoscope according to first and second embodiments.

As shown in FIG. 1, an endoscope 10 includes an elongate insertion portion 12, and an operation portion 14 provided at the proximal end of the insertion portion 12. An observation optical system and an illumination optical system that are not shown are provided inside the endoscope 10 as in a normal endoscope. An unshown channel is preferably formed in the endoscope 10.

The insertion portion 12 includes a distal rigid portion 22, a first bending portion 24, a second bending portion 26, and a flexible tubular portion 28 from the distal side to the proximal side in order. The proximal end of the flexible tubular portion 28 is coupled to the operation portion 14.

Figure 2A:
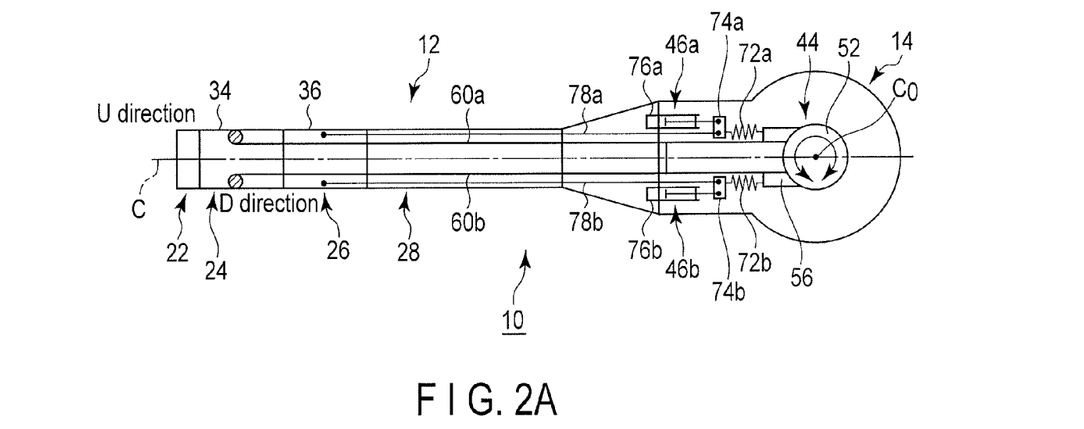
FIG. 2A is a schematic diagram showing first and second bending drive mechanisms of the endoscope according to the first embodiment in which first and second bending portions are in a straight state.
Figure 2B:
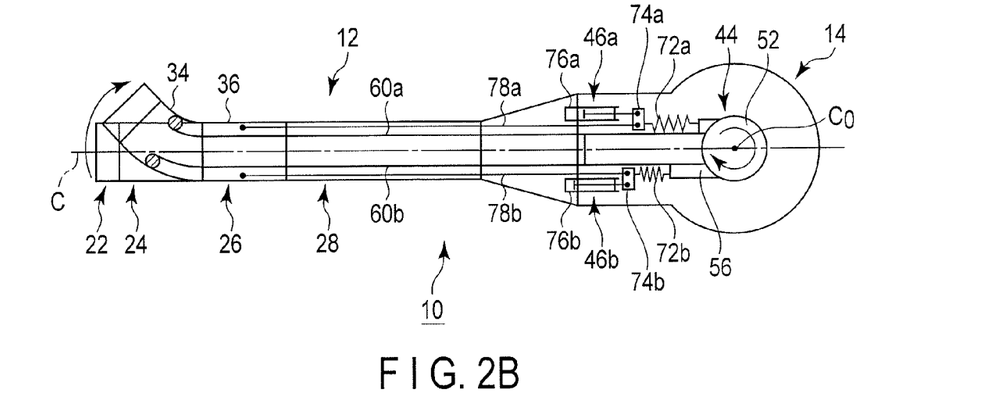
FIG. 2B is a schematic diagram showing the first and second bending drive mechanisms of the endoscope according to the first embodiment in which the first bending portion is bent in a U-direction.
Figure 2C:
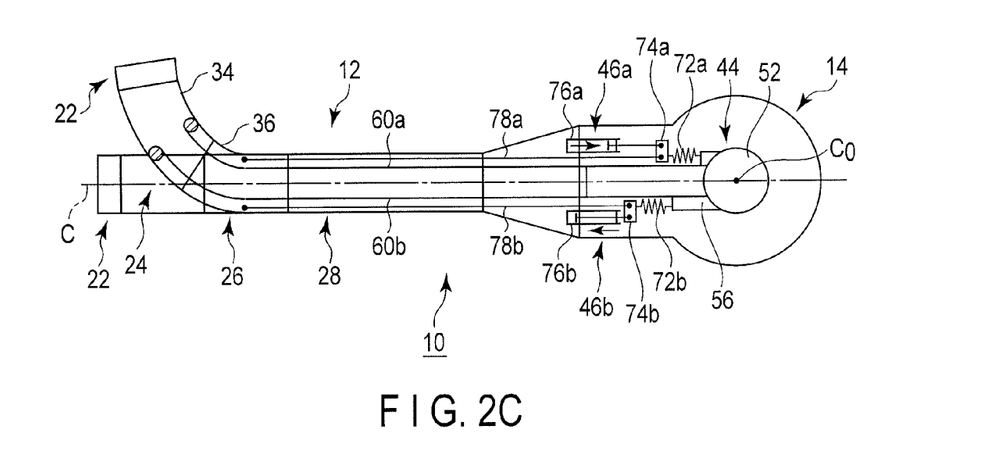
FIG. 2C is a schematic diagram showing the first and second bending drive mechanisms of the endoscope according to the first embodiment in which the second bending portion is bent in the U-direction in conformity to the first bending portion.

As shown in FIG. 2A to FIG. 2C, the first bending portion 24 includes a first bending tube 34 in which a plurality of bending pieces (not shown) are axially arranged. The second bending portion 26 includes a second bending tube 36 in which a plurality of bending pieces (not shown) are axially arranged. The first bending portion 24 and the second bending portion 26 include, for example, a braid (not shown) provided outside the first bending tube 34 and the second bending tube 36, and an outer tube provided outside the braids.

As shown in FIG. 2A to FIG. 3C, the operation portion 14 includes a first bending drive mechanism 44 for bending the first bending portion 24, and second bending drive mechanisms 46a and 46b for bending the second bending portion 26.

Figure 3A:
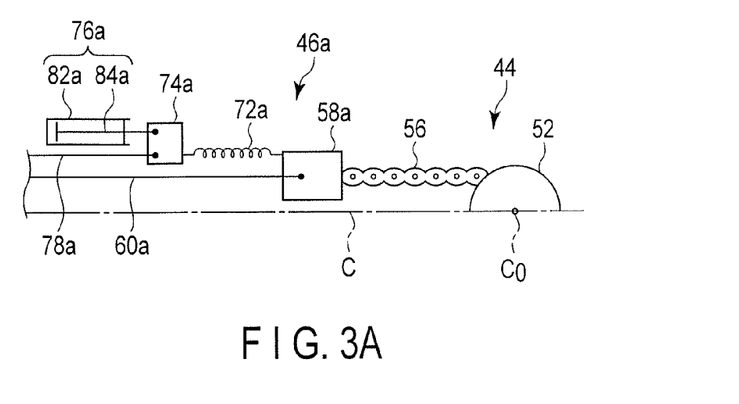
FIG. 3A is a schematic diagram showing the first and second bending drive mechanisms inside an operation portion of the endoscope according to the first embodiment in which the first and second bending portions are in a straight state.

The first bending drive mechanism 44 includes a sprocket (chain drum) 52 disposed inside the operation portion 14, a first bending portion operation knob (bending operation input portion) 54 which rotates the sprocket 52 around its central axis C0, a chain 56 engaged with and wound around the sprocket 52, first connecting members 58a and 58b disposed at the ends of the chain 56, and first angle wires 60a and 60b.

The sprocket 52 and the first bending portion operation knob 54 move, for example, integrally relative to the operation portion 14. Therefore, the operation amount of the first bending portion operation knob 54 is reflected in the sprocket 52. The first angle wires 60a and 60b have the distal ends thereof fixed to the distal end of the first bending tube 34 of the first bending portion 24, and the proximal ends thereof fixed to the first connecting members 58a and 58b.

The second bending drive mechanisms 46a and 46b have springs (elastic members) 72a and 72b fixed on one end to the first connecting members 58a and 58b, second connecting members 74a and 74b to which the other ends of the springs 72a and 72b are fixed, dampers (shock absorbers) 76a and 76b as damping devices, second angle wires 78a and 78b, and the second bending tube 36.

When the first bending portion 24 and the second bending portion 26 are straight (when the first bending portion 24 and the second bending portion 26 are on the central axis C in FIG. 2A to FIG. 2C), the springs 72a and 72b have, for example, natural lengths.

The distal ends of the second angle wires 78a and 78b are fixed to the distal end of the second bending tube 36 of the second bending portion 26, and the proximal ends of the second angle wires 78a and 78b are fixed to the second connecting members 74a and 74b.

The dampers 76a and 76b includes cylinders 82a and 82b containing, for example, silicone oil (which may be a fluid such as a gas as well as an oil (liquid)), and shafts (piston rods) 84a and 84b as movable bodies which axially move relative to the cylinders 82a and 82b. The cylinders 82a and 82b are fixed to the inside of the operation portion 14 by a jig 90 (see FIG. 5). The axial directions of the shafts 84a and 84b of the dampers 76a and 76b are preferably parallel to the axial directions of the second angle wires 78a and 78b. Thus, the shafts 84a and 84b of the dampers 76a and 76b move relative to the operation portion 14.

When the shafts 84a and 84b of the dampers 76a and 76b are moved (pulled) from the insertion portion 12 toward the operation portion 14, more force is required than when the shafts 84a and 84b are moved (pushed) from the operation portion 14 toward the distal end of the insertion portion 12. Therefore, to bend the second bending portion 26 in conformity to the first bending portion 24, the bending velocity is lower when the second bending portion 26 is bent in a direction that increases its bending angle than when the second bending portion 26 is bent in a direction that decreases its bending angle.

The second connecting members 74a and 74b are fixed to the ends of the shafts 84a and 84b of the dampers 76a and 76b. That is, the springs 72a and 72b, the second angle wires 78a and 78b, and the shafts 84a and 84b of the dampers 76a and 76b are coupled to the second connecting members 74a and 74b.

Figure 3B:
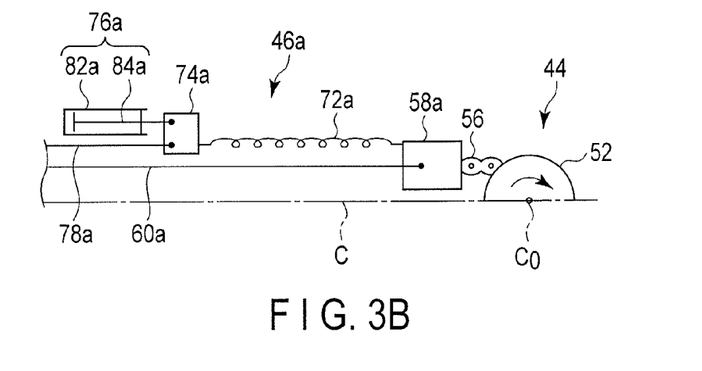
FIG. 3B is a schematic diagram showing the first and second bending drive mechanisms inside the operation portion of the endoscope according to the first embodiment in which a sprocket is rotated to bend the first bending portion in the U-direction.
Figure 3C:
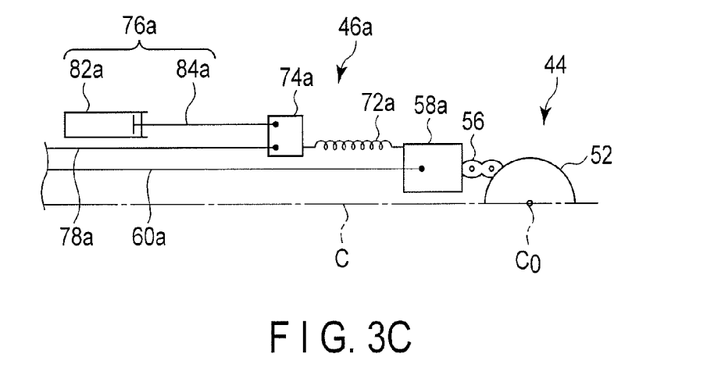
FIG. 3C is a schematic diagram showing the first and second bending drive mechanisms inside the operation portion of the endoscope according to the first embodiment in which the second bending portion is bent in the U-direction in conformity to the first bending portion.

Now, the functions of the endoscope 10 according to this embodiment are described mainly with reference to FIG. 3A to FIG. 3C.

For example, the first bending portion operation knob 54 is turned from the condition shown in FIG. 2A in which the first bending portion 24 is straight. As shown in FIG. 3A and FIG. 3B, the sprocket 52 rotates together with the first bending portion operation knob 54, and the chain 56 engaged with the sprocket 52 moves in accordance with the sprocket 52. Thus, the first angle wires 60a and 60b are axially moved by the chain 56 and the first connecting members 58a and 58b. For example, in FIG. 2B and FIG. 3B, the first angle wire 60a moves toward the operation portion 14, and although not shown, the first angle wire 60b moves toward the distal end of the insertion portion 12. Accordingly, the first bending portion 24 is bent as shown in FIG. 2B.

The first connecting member 58a are coupled to the second connecting member 74a at the end of the shaft 84a of the damper 76a via the spring 72a. Thus, the spring 72a expands relative to the natural length.

After the spring 72a has expanded relative to the natural length, force is exerted to bring the second connecting member 74a closer to the first connecting member 58a. As the cylinder 82a of the damper 76a is fixed to the operation portion 14, the shaft 84a of the damper 76a moves toward the operation portion 14. The second connecting member 74a pulls the second angle wire 78a toward the operation portion 14. At the same time, the second connecting member 74b is drawn into the distal side of the insertion portion 12 in response to the movement of the second bending portion 26.

Therefore, after the first bending portion 24 has started to bend, the second bending portion 26 bends in the same direction as the bending direction of the first bending portion 24 in conformity to the first bending portion 24. That is, the second bending drive mechanisms 46a and 46b automatically bend the second bending portion 26 in conformity to the first bending portion 24 after the start of the bending of the first bending portion 24.

The moving velocity of the shafts 84a and 84b is determined by the rotation velocity of the first bending portion operation knob 54 (the moving velocity of the chain 56) and the strength of the springs 72a and 72b.

If the first bending portion operation knob 54 is turned so that the first bending portion 24 will be straight, the sprocket 52 rotates and the chain 56 moves, the spring 72a is restored to the natural length, and the spring 72b expands.

After having expanded, the spring 72b exerts force to bring the second connecting member 74b closer to the first connecting member 58b. As the cylinder 82b of the damper 76b is fixed to the operation portion 14, the shaft 84b of the damper 76b moves toward the side of the operation portion 14. The second connecting member 74b pulls the second angle wire 78b toward the operation portion 14. The second connecting member 74a is drawn into the distal side of the insertion portion 12 in accordance with the movement of the second bending portion 26.

Therefore, after the bending angle of the first bending portion 24 has started to decrease, the second bending portion 26 decreases its bending angle in conformity to the first bending portion 24. In this case, the bending direction of the first bending portion 24 corresponds to the bending direction of the second bending portion 26. That is, if the first bending portion 24 approaches the straight state, the second bending portion 26 also gradually approaches the straight state.

A surgeon does not need to determine the timing of bending the second bending portion 26, and the second bending portion 26 can be automatically bent in conformity to the bending of the first bending portion 24. This can improve the performance of the operation of the endoscope 10 by the surgeon.

The bending velocity of the second bending portion 26 can be lower than the bending velocity of the first bending portion 24 owing to the functions of the dampers 76a and 76b. It is therefore possible to prevent a subject from being blurred when the first bending portion 24 is curved, and easily control the position for observing the subject.

Figure 4A:
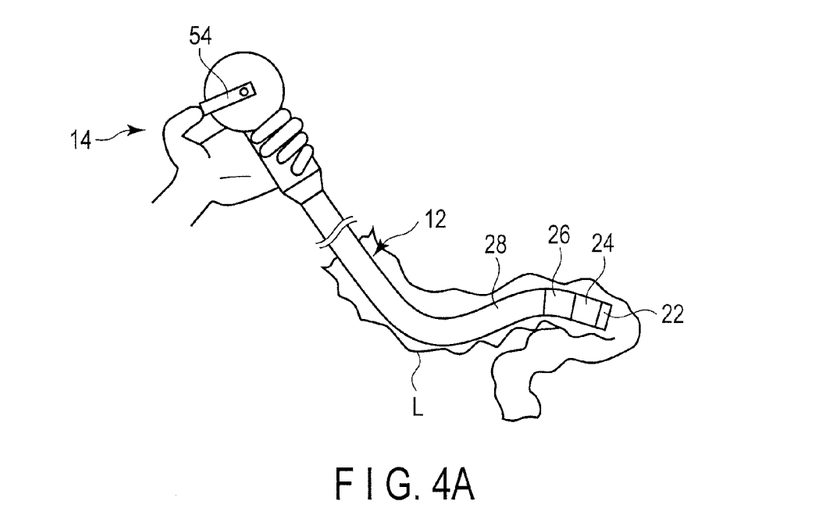
FIG. 4A is a schematic diagram showing the operation of the operation portion in which the endoscope according to the first embodiment is used to insert an insertion portion of the endoscope into a large intestine, and the movements of the first and second bending portions that bend in accordance with the operation of the operation portion, and showing how the first and second bending portions are straightened and the distal end of the insertion portion is located on the near side of a crooked region.
Figure 4B:
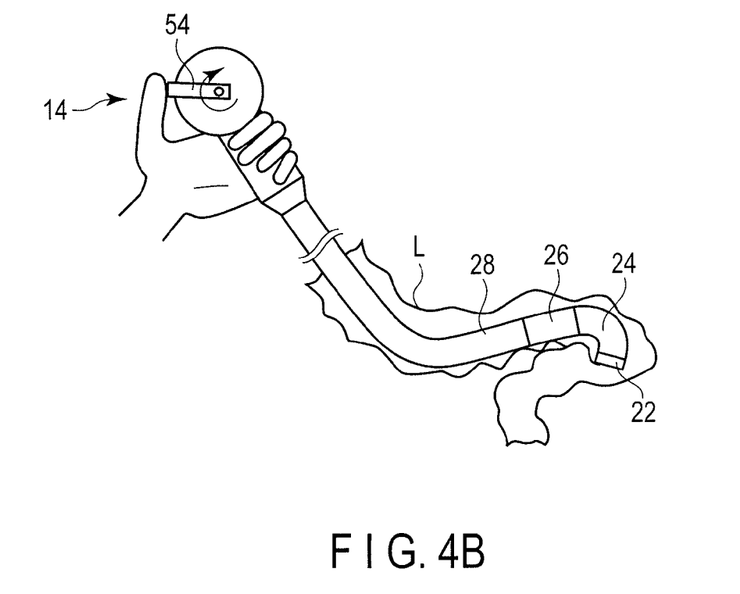
FIG. 4B is a schematic diagram showing the operation of the operation portion in which the endoscope according to the first embodiment is used to insert the insertion portion of the endoscope into the large intestine, and the movements of the first and second bending portions that bend in accordance with the operation of the operation portion, and showing how the operation portion is operated to bend the first bending portion and thereby hook the first bending portion to the crooked region.
Figure 4C:
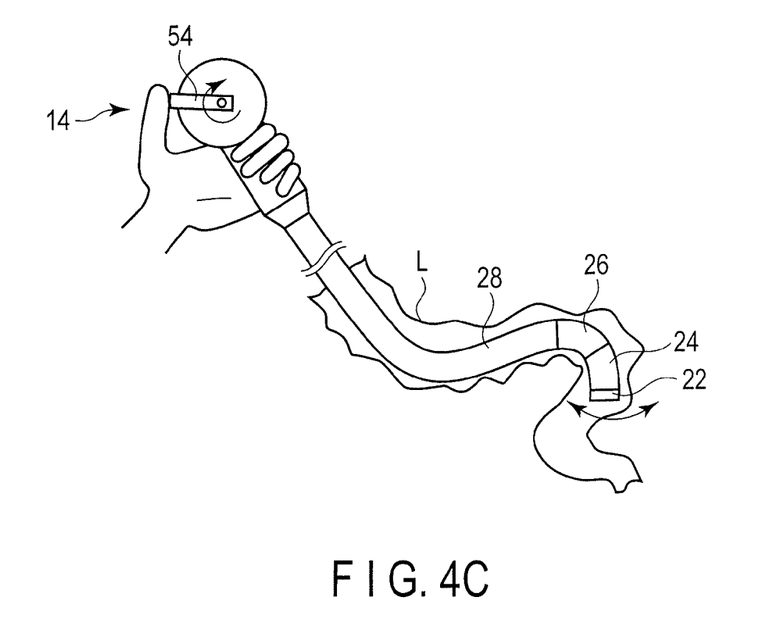
FIG. 4C is a schematic diagram showing the operation of the operation portion in which the endoscope according to the first embodiment is used to insert the insertion portion of the endoscope into the large intestine, and the movements of the first and second bending portions that bend in accordance with the operation of the operation portion, and showing how the operation portion is operated to bend the second bending portion in conformity to the first bending portion and send the first bending portion to the far side of the crooked region.

The insertion of the insertion portion 12 of the endoscope 10 into a large intestine L is briefly described with reference to FIG. 4A to FIG. 4C.

The distal end of the insertion portion 12 is inserted into the large intestine L from the anus side. At the same time, the surgeon firmly holds the insertion portion 12 with the right hand, and sends the insertion portion 12 into the far side of the large intestine L and twists the insertion portion 12, and also senses, for example, reaction force from the large intestine L to control the endoscope 10 in consideration of load on the large intestine L.

When the distal end of the insertion portion 12 has approached a crooked region of such as a sigmoid colon of the large intestine L, the surgeon bends the first bending portion 24 to hook the first bending portion 24 to the near side to far side of the crooked region. While the first bending portion 24 is bent, for example, in a U-direction, the second bending portion 26 also starts to bend in the same direction as the first bending portion 24. This ensures that the first and second bending portions 24 and 26 of the insertion portion 12 can be hooked to the near side to far side of the crooked region. At the same time, the crooked region that has been grasped by the first bending portion 24 is then grasped by the first and second bending portions 24 and 26. Accordingly, the insertion portion 12 moves to the far side relative to the crooked region.

The distal end of the insertion portion 12 is then sent to the far side of the large intestine L so that the curved first bending portion 24 is restored to the straight state. In this way, the distal end of the insertion portion 12 can be moved to the far side from the crooked region.

As described above, to increase and decrease the bending angle of the first bending portion 24, that is, to bend the first bending portion 24, the first bending portion 24 first starts to bend, and the second bending portion 26 then starts to automatically bend in the same direction as the bending direction of the first bending portion 24 after the first bending portion 24 has started to bend.

In this case, the left hand is only needed to operate the operation portion 14, and it is not necessary to take the right hand off the insertion portion 12. Thus, as the insertion portion 12 can be kept held by the right hand, the state of the insertion portion 12 relative to, for example, the large intestine L can be maintained, and the insertion portion 12 of the endoscope 10 can be moved to the far side of the large intestine L by simple operation.

The endoscope 10 according to this embodiment has not one bending portion but the two bending portions 24 and 26 for a given axial length. That is, the endoscope 10 according to this embodiment has the two bending tubes 34 and 36 within a given range. Therefore, the bending radius of each of the bending portions 24 and 26 can be smaller than that when one bending portion having the combined lengths of the bending portions 24 and 26 is formed. Consequently, the endoscope 10 according to this embodiment is particularly advantageous to the insertion of the insertion portion 12 into the far side of a part having a small corner radius.

Although the sprocket 52 and the chain 56 are used in the example described in this embodiment, a pulley to which a wire is directly fixed via first connecting members 58a and 58b for connecting the first angle wires 60a and 60b may be used instead.

The dampers 76a and 76b may be either what is known as a single cylinder type or a multiple cylinder type. For example, a stretchable rubber material is also preferably used as an elastic member instead of the springs 72a and 72b.

Moreover, various members that allow the angle wires 78a and 78b to be laid in accordance with the expansion and compression of the springs 72a and 72b can be used as damping devices instead of the dampers 76a and 76b.

Although the first bending portion 24 is bent in the vertical direction (U- and D-directions) in the endoscope 10 shown in FIG. 1 in the case described above, the first bending portion 24 may be configured to be bent in the U- and D-directions and the horizontal direction (R- and L-directions).

Figure 5:
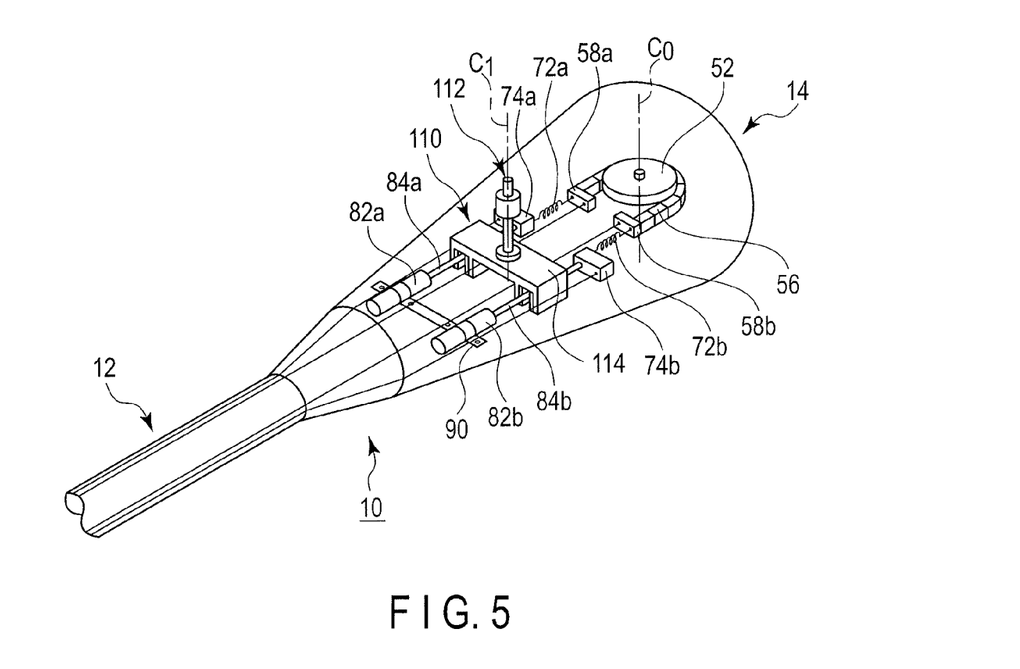
FIG. 5 is a schematic perspective view showing the first and second bending drive mechanisms inside the operation portion of the endoscope according to the first embodiment, and a switch mechanism.
Figure 6A:
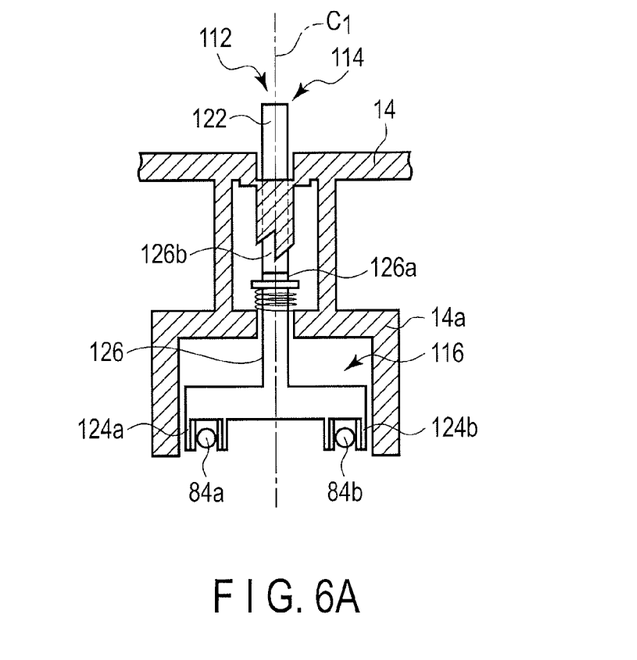
FIG. 6A is a schematic cross-sectional view showing the switch mechanism inside the operation portion of the endoscope according to the first embodiment, and showing how the second bending portion is prevented from conforming to the first bending portion even if the operation portion is operated.
Figure 6B:
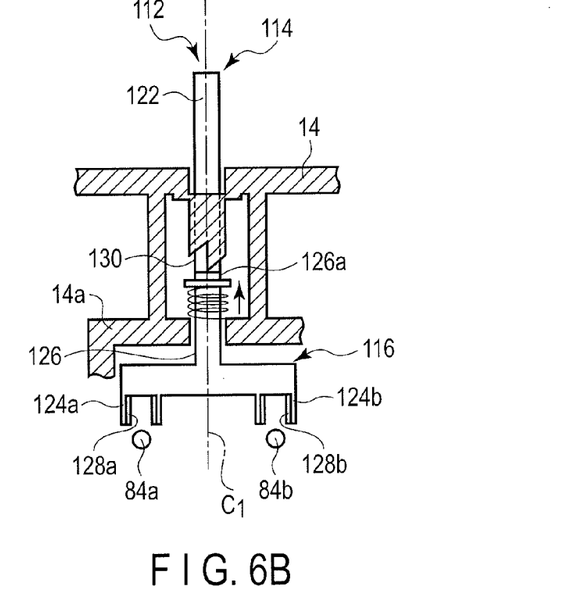
FIG. 6B is a schematic cross-sectional view showing the switch mechanism inside the operation portion of the endoscope according to the first embodiment, and showing how the second bending portion is bent in conformity to the bending of the first bending portion.

In the meantime, as shown in FIG. 5 to FIG. 6B, a switch mechanism 110 is preferably provided in the operation portion 14 of the endoscope 10 to switch between a first condition in which the second bending portion 26 is bent in conformity to the first bending portion 24 and a second condition in which the second bending portion 26 is not bent or is not easily bent even when the first bending portion 24 is bent.

The switch mechanism 110 has a stopper mechanism 112 that uses a knock-type structure widely used in, for example, ball-point pens.

As shown in FIG. 6A and FIG. 6B, the stopper mechanism 112 includes a knock portion 114 supported by the operation portion 14, and a movable member 116 which is disposed inside the operation portion 14 and which moves in accordance with the movement of the knock portion 114. The knock portion 114 is disposed to penetrate the operation portion 14 from the inside to the outside. A shaft-like knock body (shaft body) 122 of the knock portion 114 projects out of the operation portion 14. The knock body 122 is disposed in the vicinity of the first bending portion operation knob 54, and the knock body 122 and the first bending portion operation knob 54 can be operated with the left hand alone. The knock body 122 is preferably located to be operable when a finger other than the thumb operating the first bending portion operation knob 54 is extended to the knock body 122.

The direction of the central axis C1 of the knock body 122 is preferably parallel to the rotation center C0 of the sprocket 52.

The knock body 122 can be switched between a condition (second condition) in which the knock body 122 is pushed into the operation portion 14 as shown in FIG. 6A and a condition (first condition) in which the operation portion 14 projects out of the operation portion 14 as shown in FIG. 6B. The amount of the projection of the knock body 122 from the outer surface of the operation portion 14 is preferably about several millimeters to one centimeter. For example, the knock body 122 is airtightly and liquid-tightly covered by an unshown cover member outside the operation portion 14 so that a fluid is not let in or out of the operation portion 14.

The movable member 116 includes two constraining portions 124a and 124b which can constrain/release the two shafts 84a and 84b of the dampers 76a and 76b at the same time, and a shaft 126. The shaft 126 includes a rotary shaft 126a between one end (upper end) and the other end (lower end). The constraining portions 124a and 124b are substantially U-shaped in cross section, and include, in the inner peripheral surface thereof, for example, rubber friction load members 128a and 128b which apply friction force to regulate the axial movement of the shafts 84a and 84b of the dampers 76a and 76b.

A stopper 126b is formed in the shaft 126 closer to one end than the rotary shaft 126a, and can engage with and disengage from an inclined plane 130 formed in an inner frame 14a of the operation portion 14.

The movement of the movable member 116 around the axis of the knock body 122 is regulated by the inner frame 14a of the operation portion 14. When the movable member 116 is forcibly rotated around the axis of the knock body 122 due to the structure of the knock portion 114, the movement of the constraining portions 124a and 124b in the rotation direction can be regulated by the rotary shaft 126a of the shaft 126 and the inner frame 14a of the operation portion 14.

The movement of the movable member 116 in the axial direction of the two shafts 84a and 84b of the dampers 76a and 76b is also regulated by the inner frame 14a of the operation portion 14.

If the knock body 122 of the knock portion 114 is pressed toward the inside of the operation portion 14, the inclined plane 130 of the inner frame 14a engages with the stopper 126b. That is, if the knock body 122 of the knock portion 114 is pressed toward the inside of the operation portion 14, the movable member 116 moves toward the shafts 84a and 84b of the dampers 76a and 76b together with the knock portion 114. Thus, the two shafts 84a and 84b of the dampers 76a and 76b are held and constrained by the constraining portions 124a and 124b. At the same time, the movement of the movable member 116 in the axial direction of the two shafts 84a and 84b of the dampers 76a and 76b is also regulated, so that it is possible to prevent the second bending portion 26 from bending in the same direction as the first bending portion 24.

On the other hand, when the knock body 122 of the knock portion 114 is operated so that the knock body 122 projects out of the operation portion 14, the stopper 126b is disengaged from the inclined plane 130a, and the stopper 126b moves to the rear surface in FIG. 6B. Therefore, when the knock portion 114 is projected out of the operation portion 14, a state that the shafts 84a and 84b of the dampers 76a and 76b are held and constrained by the constraining portions 124a and 124b can be released. As a result, the second bending portion 26 can be bent in conformity to the first bending portion 24.

If the knock body 122 is operated while the first bending portion operation knob 54 is being operated or after the operation of the first bending portion operation knob 54 is stopped, the springs 72a and 72b can be kept expanded or compressed relative to the natural length. For example, if the knock body 122 is further operated when one spring 72a is expanded and the other spring 72b is compressed, force is rapidly applied to the shafts 84a and 84b of the dampers 76a and 76b by the urging force of the springs 72a and 72b, but the moving velocity of the shafts 84a and 84b is much lower than the velocity at which the springs 72a and 72b are compressed when released from the condition expanded at the free ends. The movement of the shafts 84a and 84b in the pulling direction of the second angle wires 78a and 78b is slower than the movement in the pushing direction. Therefore, the rapid increase of the bending angle of the second bending portion 26 can be prevented by the dampers 76a and 76b.

The switch mechanism 110 is thus disposed in the operation portion 14 so that a user of the endoscope 10 can switch (select) whether to conform the second bending portion 26 to the first bending portion 24. Therefore, the function to bend the second bending portion 26 in conformity to the first bending portion 24 can be switched, for example, in accordance with a part (e.g. the large intestine L) into which the insertion portion 12 is inserted and in accordance with a patient.

Even while the first bending portion 24 is being bent or after the first bending portion 24 has been bent, the switch mechanism 110 can be operated to further bend the second bending portion 26 in the same direction as the bending direction of the first bending portion 24 in conformity to the first bending portion 24 or decrease the bending angle of the second bending portion 26.

The switch mechanism 110 is not limited to the knock-type structure, and allows for various structures that can constrain/release the two shafts 84a and 84b of the dampers 76a and 76b. Moreover, the switch mechanism 110 is not limited to the various structures that can constrain/release the two shafts 84a and 84b, and allows for a structure that can regulate/ deregulate the movement of the second connecting members 74a and 74b, or a structure that can prevent the expansion and compression of the springs 72a and 72b.

Now, the second embodiment is described with reference to FIG. 7 and FIG. 8. This embodiment is a modification of the first embodiment, and the same components as the components described in the first embodiment are indicated by the same reference signs, and are not described in detail.

In this embodiment, later-described motors 212a and 212b are used as the damping devices instead of the springs 72a and 72b and the dampers 76a and 76b.

Figure 7:
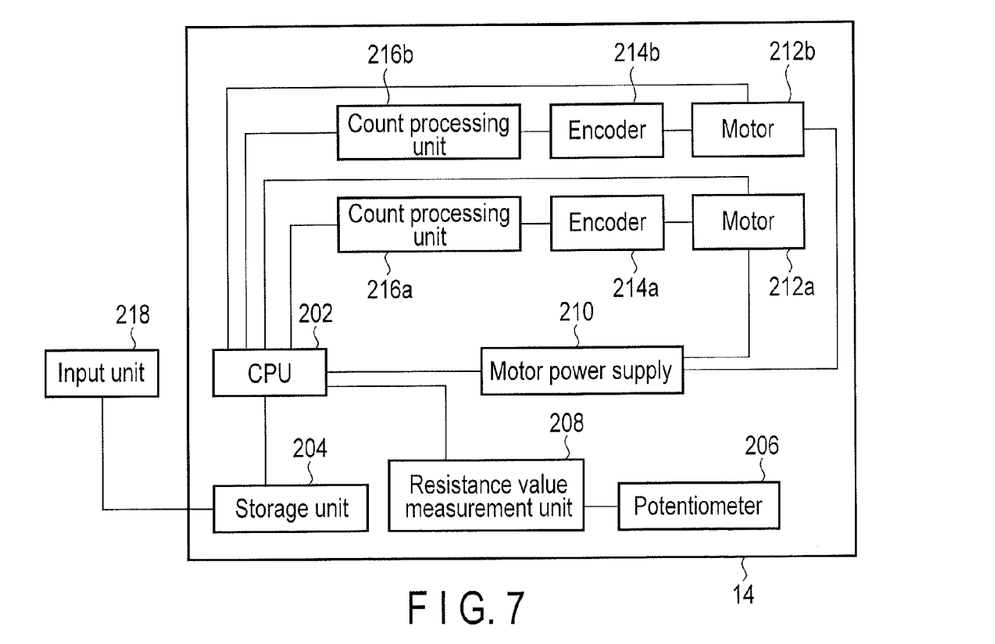
FIG. 7 is a schematic block diagram of a device disposed inside an operation portion of the endoscope according to the second embodiment.
Figure 8:
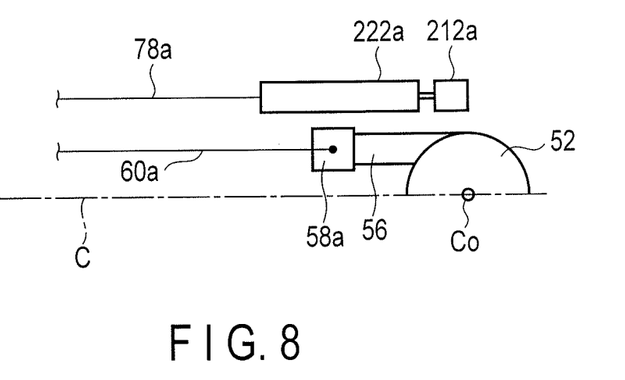
FIG. 8 is a schematic diagram showing first and second bending drive mechanisms inside the operation portion of the endoscope according to the second embodiment.

As shown in FIG. 7, the operation portion 14 is provided with a CPU 202, a storage unit 204, a potentiometer (position sensor) 206, a resistance value measurement unit 208, a motor power supply 210, the motors 212a and 212b, encoders 214a and 214b, count processing units 216a and 216b, and an input unit 218. The CPU 202, the storage unit 204, the potentiometer 206, the resistance value measurement unit 208, the motor power supply 210, the motors 212a and 212b, the encoders 214a and 214b, and the count processing units 216a and 216b are preferably provided inside the operation portion 14, the input unit 218 may be removable from the operation portion 14.

Linear motors (e.g. ultrasonic motors) or direct-current/alternating-current motors having rotational drive shafts may be used as the motors 212a and 212b. When the direct-current/alternating-current motors are used, the rotary motion of the drive shaft of the motor 212a is converted to linear motion via a ball screw 222a to the drive shaft of one motor 212a, as shown in FIG. 8. The angle wire 78a can be then axially moved. Although not shown, the rotary motion of the drive shaft of the motor 212b is converted to linear motion via a ball screw 222b to the drive shaft of the other motor 212b.

The potentiometer (input amount detector) 206 is attached to the sprocket 52. By setting the potentiometer 206 in accordance with the initial position (position that allows the first bending portion 24 to be straight) of the first bending portion operation knob 54, the potentiometer 206 can detect the rotation amount of the sprocket 52, that is, the rotational position (rotation angle) of the first bending portion operation knob 54.

The rotational position of the first bending portion operation knob 54, that is, the rotation amount of the sprocket 52 substantially corresponds to the bending amount of (bending angle) of the first bending portion 24 in the U-direction and D-direction. Thus, the potentiometer 206 can be used to estimate the bent state of the first bending portion 24 in the U- and D-directions in accordance with the rotation amount of the first bending portion operation knob 54.

The motors 212a and 212b are then driven when the first bending portion 24 has exceeded a given threshold input by the input unit 218 and stored in the storage unit 204.

The motors (driving portions) 212a and 212b, and the encoders (rotational position detectors) 214a and 214b for detecting the rotation amounts (rotation angles) of the motors 212a and 212b are disposed in the operation portion 14. The motors 212a and 212b generate driving force to bend the second bending portion 26. Therefore, the second bending tube 36, the wires 78a and 78b, the motors 212a and 212b, and the ball screws 222a and 222b form the second bending drive mechanisms 46a and 46b for bending the second bending portion 26.

The encoders 214a and 214b are provided in the motors 212a and 212b, and the driving amounts (e.g. rotation amounts) of the motors 212a and 212b can be obtained in accordance with measurements by the encoders 214a and 214b.

The input unit 218 inputs (sets), for example, parameters (thresholds) necessary to automatically bend the second bending portion 26 in conformity to the first bending portion 24.

After the bending of the first bending portion 24 has been started, the input unit 218 can set the timing for actuating the motors 212a and 212b to bend the second bending portion 26. For example, by setting a threshold in the input unit 218, the second bending portion 26 can be bent in the same direction as the bending direction of the first bending portion 24 when the first bending portion 24 has become equal to or more than a predetermined bending angle.

The input unit 218 can set a conforming velocity when the second bending portion 26 is curved. For example, when the second bending portion 26 is curved, the time required to bend the second bending portion 26 to a given angle $\alpha$ can be controlled to be longer than the time required to curve the first bending portion 24 to the given angle $\alpha$.

The input unit 218 can set the second bending portion 26 so that the second bending portion 26 is not curved (the motors 212a and 212b are not driven) even when the first bending portion 24 is curved. That is, it is possible to select whether to curve the second curving portion 26 in conformity to the first curving portion 24 or prevent the second curving portion 26 from conforming to the first curving portion 24 even if the first bending portion 24 is curved. For this changeover, a changeover switch may be provided in addition to the input unit 218. If the changeover switch is operated while the first bending portion 24 is being bent, the second bending portion 26 can be bent in conformity to the first bending portion 24.

The input unit 218 may be provided in the operation portion 14, or may be removable from the operation portion 14. It is also preferable that the input unit 218 enables various settings through radio communication by an unshown radio communication system which is removable from the operation portion 14 or which is disposed inside the operation portion 14.

While the first bending portion 24 is being bent and stopped at a given bending angle, the conforming velocity at which to bend the second bending portion 26 can be properly set by the input unit 218 to suit to the surgeon's preferences.

The motors 212a and 212b are driven in accordance with the rotational position of the first bending portion operation knob 54. The bending angle of the second bending portion 26 is reduced when the rotation amount of the first bending portion operation knob 54 is small (the bending angle of the first bending portion 24 is small), and the bending angle of the second bending portion 26 is increased when the rotation amount is great (the bending angle of the first bending portion 24 is great). In this case, the bending angle of the second bending portion 26 is preferably smaller than the bending angle of the first bending portion 24. That is, it is preferable to prevent the bending angle of the second bending portion 26 from being greater than the bending angle of the first bending portion 24.

It is also preferable that a position sensor (not shown) is provided in, for example, the first connecting members 58a and 58b instead of the potentiometer 206 disposed in at least one of the first bending portion operation knob 54 and the sprocket 52 to calculate the bending angle of the first bending portion 24. Otherwise, the position sensor may be provided in, for example, the chain 56.

While several embodiments have so far been described in detail with reference to the drawings, this invention is not limited to the embodiments described above, and covers all embodiments carried out without departing from the spirit of the invention.

[Addition]

1. An endoscope is characterized by includes an insertion portion which includes a first curving portion and a second curving portion disposed at the proximal end of the first curving portion; a curving operation input portion which curves the first curving portion; a first curving drive mechanism which curves the first curving portion in accordance with the operation of the curving operation input portion; and a second curving drive mechanism which automatically curves the second curving portion in the same direction as the curving direction of the first curving portion in conformity to the first curving portion after the start of the curving of the first curving portion.

Thus, the second curving portion can automatically conform to the first curving portion in the same direction as the curving direction of the first curving portion after the start of the curving of the first curving portion, so that the user of the endoscope can use the endoscope without considering the operation of the second curving portion. As the second curving portion is curved after the start of the curving of the first curving portion, it is possible to prevent the difficulty of finding an observation target of the curving portion. That is, it is possible to provide an endoscope having a plurality of curving portions which allows the curving portions to be readily curved only by one-handed operation and which can prevent the difficulty of finding an observation target.

2. Preferably, the second curving drive mechanism includes an elastic member coupled to the first curving drive mechanism, a damping device having a shaft which is coupled to the elastic member and which is movable by smaller force when moved in a direction to approach the first and second curving portions than when moved away from the first and second curving portions, and an angle wire coupled to the shaft of the damping device.

Therefore, the elastic member is expanded and compressed together with the first curving drive mechanism, and the shaft is moved by elastic force of the elastic member, thereby moving the angle wire of the second curving portion so that the second curving portion can be automatically curved in conformity to the first curving portion.

3. Preferably, the endoscope further includes a switch mechanism which switches between an interlock condition to interlock the second curving drive mechanism with the operation of the first curving drive mechanism and a non-interlock condition to stop the operation of the second curving drive mechanism to release the interlock of the second curving drive mechanism with the first curving drive mechanism.

In this case, the user of the endoscope can operate the switch mechanism to switch whether or not to automatically curve the second curving portion in conformity to the first curving portion. It is also possible to release the interlock condition or switch from the non-interlock condition to the interlock condition by operating the switch mechanism in the process of curving the first curving portion.

4. Preferably, the second curving drive mechanism includes a pair of angle wires, and a driving portion which is coupled to at least one of the curving operation input portion and the first curving drive mechanism and also coupled to the angle wires of the second curving drive mechanism and which more slowly drives the angle wires when moving the angle wires in a direction to approach the first and second curving portions than when moving the angle wires away from the first and second curving portions.

As the driving portion is coupled to at least one of the curving operation input portion and the first curving drive mechanism, the second curving portion can be automatically curved in conformity to the first curving portion after the start of the curving of the first curving portion.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
   an insertion portion which includes a first bending portion and a second bending portion provided at the proximal end of the first bending portion;
   a first traction wire with one end coupled to the first bending portion, the first traction wire being configured to bend the first bending portion in a predetermined direction;
   an operation input portion configured to input an operation to pull the first traction wire;
   a second traction wire with one end coupled to the second bending portion, the second traction wire being configured to bend the second bending portion in a predetermined direction; and
   a bending conforming mechanism which includes one end coupled to the other end of the second traction wire and the other end coupled to the operation input portion, and which is configured to pull the second traction wire so as to bend the second bending portion at a bending velocity lower than the bending velocity of the first bending portion which is bent by a pull of the first traction wire being pulled by the input of an operation to the operation input portion and in conformity to the first bending portion after a start of the bending of the first bending portion by pulling the first traction wire.

2. The endoscope according to claim 1, wherein
   the bending conforming mechanism includes:
   a damping device which is configured to suppress the pulling velocity of the second traction wire so that the pulling velocity of the second traction wire is lower than the pulling velocity of the first traction wire when the first traction wire and the second traction wire are pulled by the input of an operation to the operation input portion, and
   an elastic member which is configured to elastically expand and generate the traction force in response to the input of the operation to the operation input portion.

3. The endoscope according to claim 2, further including a connection portion which connects the elastic member and the damping device, wherein:
   the elastic member has one end coupled to the operation input portion, and
   the second traction member is connected to the connection portion.

4. The endoscope according to claim 1, further comprising a switch mechanism which is configured to switch between an interlock condition to interlock and pull the second traction wire with the pulling operation of the first traction wire and a non-interlock condition to stop the pulling operation of the second traction wire to release the interlock and pulling of the second traction wire with the first traction wire.

5. The endoscope according to claim 4, wherein the switch mechanism is provided in the vicinity of the operation input portion.

* * * * *